United States Patent
Sgatti et al.

(10) Patent No.: US 8,555,702 B2
(45) Date of Patent: Oct. 15, 2013

(54) METHOD FOR RECOGNIZING AT LEAST ONE FEATURE OF THE FUEL IN AN INTERNAL COMBUSTION ENGINE

(75) Inventors: Stefano Sgatti, Imola (IT); Alberto Bucci, Campinas (BR); Nicolo' Cavina, Bologna (IT); Marco Cesaroni, Ascoli Piceno (IT); Filippo Cavanna, Bologna (IT); Ludovico Ausiello, Bologna (IT)

(73) Assignee: Magneti Marelli S.p.A., Corbetta (IT)

( * ) Notice: Subject to any disclaimer, the term of this patent is extended or adjusted under 35 U.S.C. 154(b) by 28 days.

(21) Appl. No.: 13/421,381

(22) Filed: Mar. 15, 2012

(65) Prior Publication Data
US 2013/0067990 A1 Mar. 21, 2013

(30) Foreign Application Priority Data
Mar. 15, 2011 (IT) .............................. BO2011A0122

(51) Int. Cl.
*G01N 33/22* (2006.01)
(52) U.S. Cl.
USPC ..................................... 73/35.02; 73/114.01
(58) Field of Classification Search
USPC ........................................... 73/35.02, 114.01
See application file for complete search history.

(56) References Cited

U.S. PATENT DOCUMENTS

| 7,421,884 | B2* | 9/2008 | Aoyama | 73/35.02 |
|---|---|---|---|---|
| 7,556,030 | B2* | 7/2009 | Ashida et al. | 123/575 |
| 7,621,174 | B2* | 11/2009 | Takaku | 73/114.53 |
| 7,926,331 | B2* | 4/2011 | Tsutsumi et al. | 73/114.38 |
| 7,987,696 | B2* | 8/2011 | Kuronita et al. | 73/35.02 |
| 8,074,503 | B2* | 12/2011 | Tsutsumi et al. | 73/114.38 |
| 8,256,281 | B2* | 9/2012 | Nishiumi | 73/114.49 |
| 8,430,082 | B2* | 4/2013 | Bohnig et al. | 123/493 |
| 2008/0257017 | A1* | 10/2008 | Ritz | 73/35.02 |
| 2010/0088008 | A1 | 4/2010 | Tanaka et al. | |
| 2010/0132435 | A1* | 6/2010 | Doring | 73/28.04 |

FOREIGN PATENT DOCUMENTS

| EP | 2128412 A1 | 12/2009 |
|---|---|---|
| JP | 2005098115 A | 4/2005 |

OTHER PUBLICATIONS

Oct. 5, 2011 Search Report for Italian Patent App. No. BO20110122.

* cited by examiner

*Primary Examiner* — Freddie Kirkland, III
(74) *Attorney, Agent, or Firm* — Howard & Howard Attorneys PLLC

(57) ABSTRACT

A method recognizes at least one feature of fuel in an internal-combustion engine (1). The method comprises steps of: detecting, by at least one sensor, intensity (S) of vibrations generated by the internal-combustion engine (1) within a measurement-time window; determining a value of at least one synthetic index (I) by processing the intensity (S) of the vibrations generated by the internal-combustion engine (1) within the measurement-time window; comparing a synthetic index (I) with at least one predetermined comparison quantity (TH); and recognizing the feature of the fuel as a function of the comparison between the synthetic index (I) and comparison quantity (TH).

Figure 1:
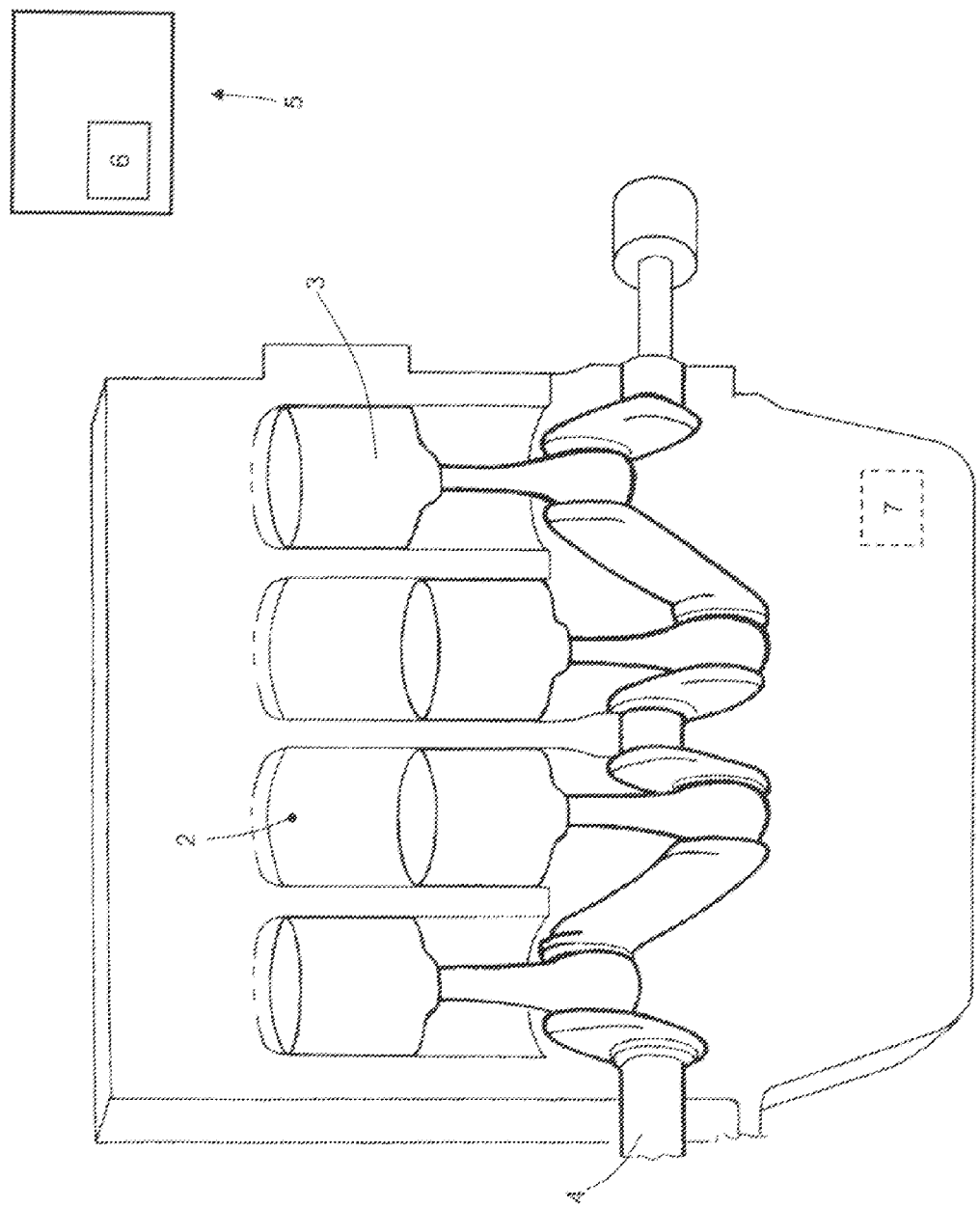

15 Claims, 3 Drawing Sheets

METHOD FOR RECOGNIZING AT LEAST ONE FEATURE OF THE FUEL IN AN INTERNAL COMBUSTION ENGINE

REFERENCE TO RELATED APPLICATION

This application claims benefit of the filing date of and priority to Italian Patent Application BO2011A 000122 filed on Mar. 15, 2011.

BACKGROUND OF INVENTION

1. Field of Invention

The present invention relates, generally, to a method for recognizing at least one feature of fuel in an internal-combustion engine.

2. Description of Related Art

In some areas of the world (e.g., Brazil), for several years now, spark-ignited internal-combustion engines may be fed with different types of liquid fuel (e.g., pure petrol, hydrate alcohol, or a mixture of petrol and alcohol) that have different features (e.g., different "air/fuel" stoichiometric ratios). Recently, modern diesel engines may use fuels other than pure diesel fuel, which fuels are commercially named "bio-diesel" and consist of a mixture of diesel fuel and bio-mass-originated fuels (e.g., vegetable oils, such as rape-seed oil).

Consequently, it is important for an electronic-control unit of the engine to know the type of fuel that is actually used by the internal-combustion engine to be able to optimize combustion control as a function of features of the fuel actually used. For example, it is fundamental to know the actual stoichiometric "air/fuel" ratio to minimize generation of pollutants, and it is very useful to know volatility to guarantee correct "cold" starting of the internal-combustion engine.

Different "fuel-type recognition" methods are based on information provided by the lambda probe present in exhaust. However, there is a need in the related art to be able to use other "fuel-type recognition" methods that do not exploit information provided by the lambda probe present at the exhaust to have a possibility of recognizing the type of fuel also in "recovery" mode when the lambda probe is not working correctly. There is a need in the related art also to have a possibility of comparing the fuel-type recognition performed starting from the information provided by the lambda probe with another independent recognition to increase recognition confidence.

SUMMARY OF INVENTION

The invention overcomes the disadvantages in the related art in a method for recognizing at least one feature of fuel in an internal-combustion engine (1). The method comprises steps of: detecting, by at least one sensor, intensity (S) of vibrations generated by the internal-combustion engine (1) within a measurement-time window; determining a value of at least one synthetic index (I) by processing the intensity (S) of the vibrations generated by the internal-combustion engine (1) within the measurement-time window; comparing a synthetic index (I) with at least one predetermined comparison quantity (TH); and recognizing the feature of the fuel as a function of the comparison between the synthetic index (I) and comparison quantity (TH).

One advantage of the method for recognizing at least one feature of fuel in an internal-combustion engine of the invention is that it does not use information supplied by a lambda probe present at exhaust.

Another advantage of the method for recognizing at least one feature of fuel in an internal-combustion engine of the invention is that it is both easy and cost-effective to implement.

Other objects, features, and advantages of the method for recognizing at least one feature of fuel in an internal-combustion engine of the invention are readily appreciated as the method become more understood while the subsequent detailed description of at least one embodiment of the method is read taken in conjunction with the accompanying drawing thereof.

BRIEF DESCRIPTION OF EACH FIGURE OF DRAWING

Figure 2:
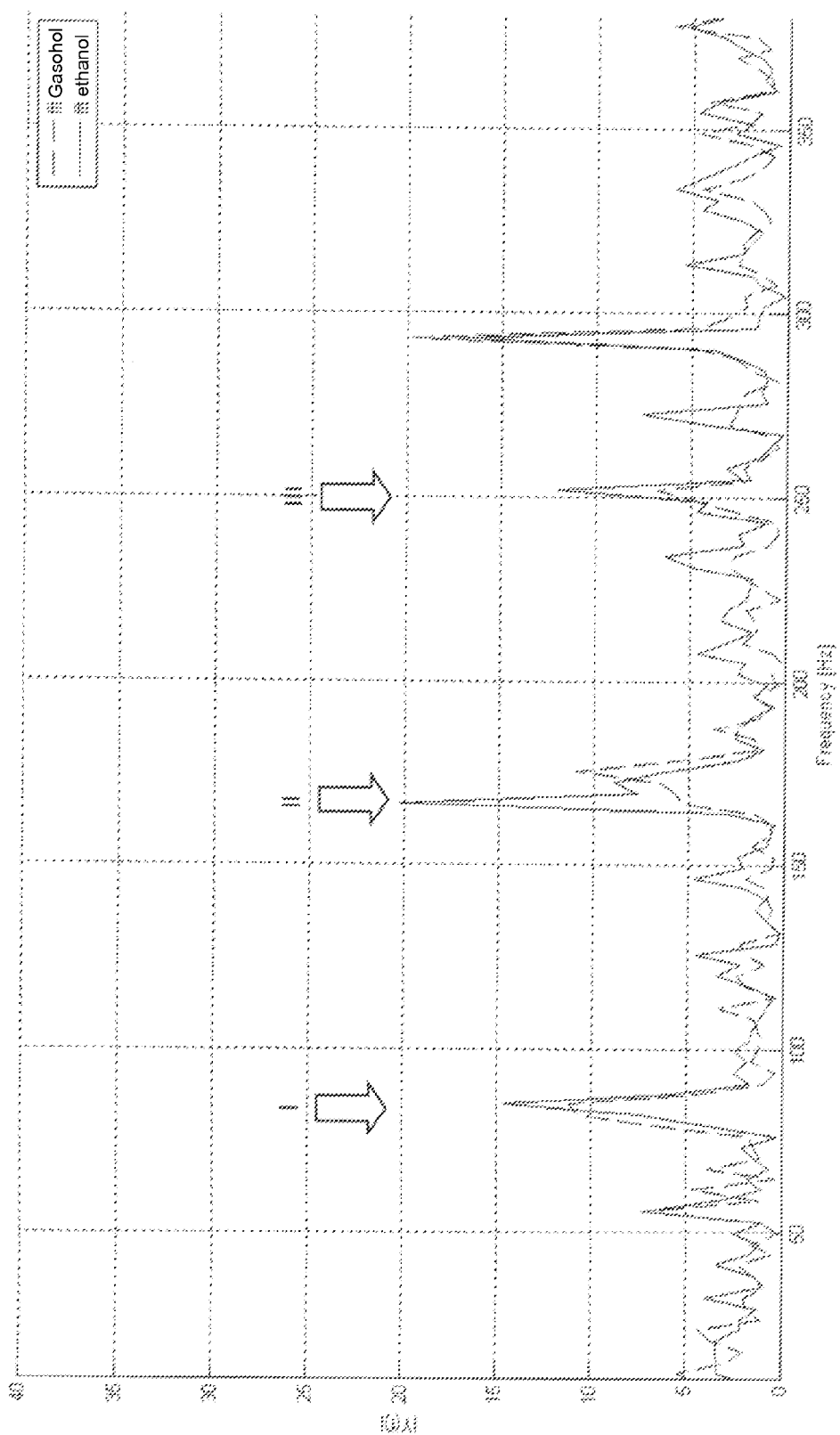
Figure 3:
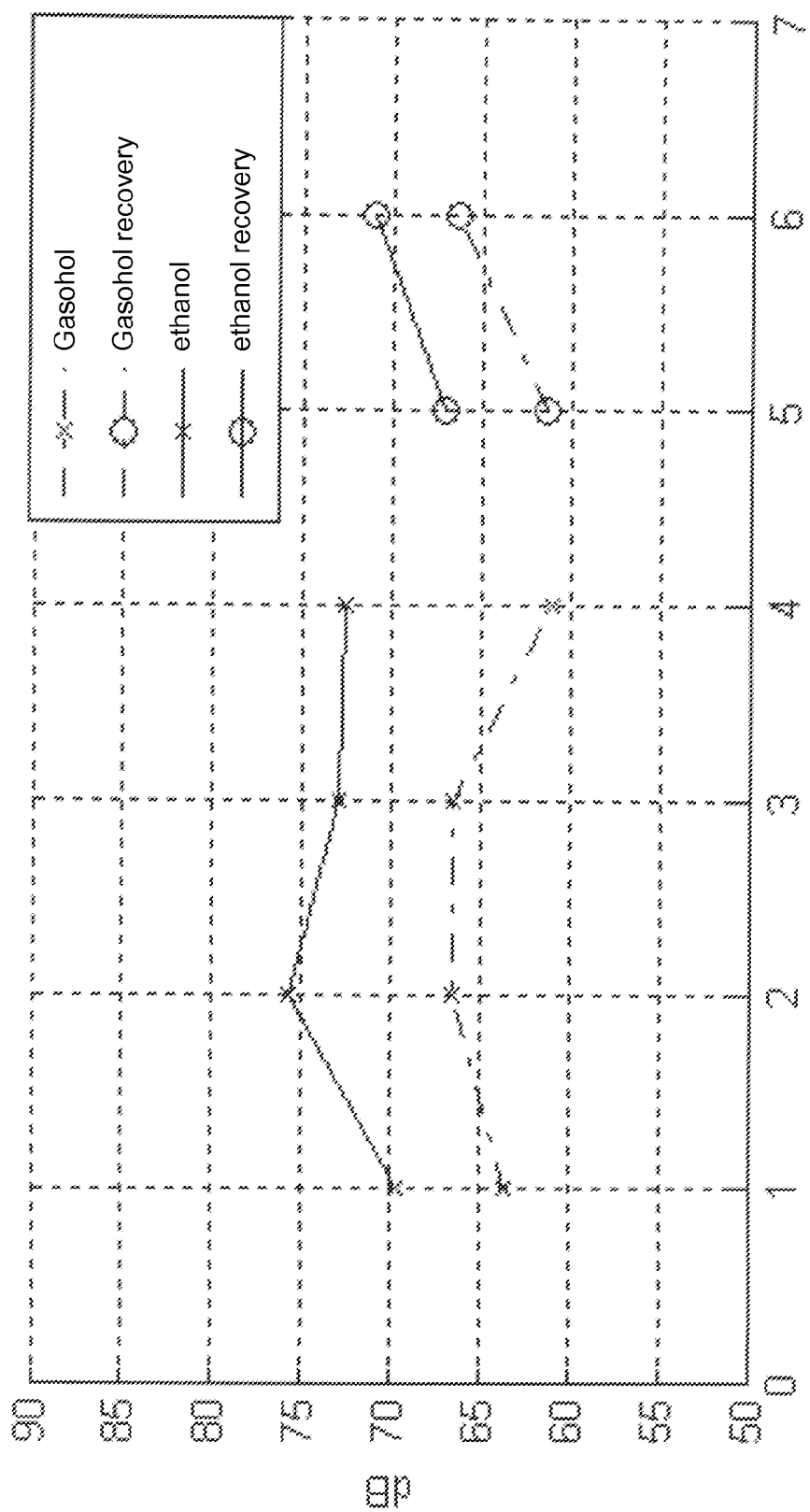

FIG. 1 is a diagrammatic view of an internal-combustion engine provided with a control unit that implements the method for recognizing at least one feature of fuel in an internal-combustion engine of the invention;

FIG. 2 is a chart illustrating FFT of noise generated by the internal-combustion engine in FIG. 1 when the internal-combustion engine itself uses two different types of fuel; and FIG. 3 is a graph that illustrates a pattern of a synthetic index determined as a function of the FFT of the noise generated by the internal-combustion engine in FIG. 1 when the internal-combustion engine uses two different fuel types in different engine points.

DETAILED DESCRIPTION OF EMBODIMENT(S) OF INVENTION

In FIG. 1, an internal-combustion engine is generally indicated at 1 and comprises four cylinders 2 in straight arrangement. Each cylinder 2 comprises a piston 3 mechanically connected by a connecting rod to a drive shaft 4 for transmitting force generated by combustion in the cylinder 2 to the drive shaft 4 itself.

The internal-combustion engine 1 is governed by an electronic-control unit (normally named "ECU") that is arranged near the internal-combustion engine 1 and normally accommodated in an engine compartment of a vehicle (not shown). The electronic-control unit 5 comprises a microphone 6 (i.e., an "'acoustic' type" pressure sensor 6) that is accommodated within the control unit 5 and adapted to detect intensity of noise (i.e., recognize intensity of "acoustic," "sound," and "pressure" waves) generated by the internal-combustion engine 1.

In use, the electronic-control unit 5 detects, by the microphone 6, the intensity "S" of the noise (i.e., vibrations) generated by the internal-combustion engine 1 in a measurement-time window of a given amplitude (normally in the order of 0.1-0.5 second). In the electronic-control unit 5, the intensity "S" of the noise generated by the internal-combustion engine 1 is digitalized using a relatively high-frequency sampling (in the order of 50 kHz). Subsequently, the electronic-control unit 5 determines the value of at least one synthetic index "I" by processing the intensity "S" of the noise generated by the internal-combustion engine 1 in the measurement-time window. The synthetic index "I" is compared with at least one predetermined comparison quantity "TH," and, thus, a feature (i.e., the composition) of the fuel used by the internal-combustion engine 1 is recognized as a function of the comparison between the synthetic index "I" and the comparison quantity "TH." The comparison quantity "TH" is experimentally determined during a step of calibrating performed by feeding fuels having different known features to the internal-combustion engine 1 appropriately provided with laboratory instruments.

Normally, the comparison quantity "TH" is associated with a given recognition-operating point of the internal-combustion engine 1. In other words, the comparison quantity "TH" is determined in the recognition-operating point and is, thus, only valid at the recognition-operating point itself. The operating point of the engine 1 (also referred to as "the engine point") is generally identified by a revolution-rate value and load value (provided by the aspiration pressure or efficiency, i.e., the ratio between the amount of air actually aspirated and the maximum amount of air that may be aspirated). The synthetic index "I" and comparison quantity "TH" are only compared when the current operating point of the internal-combustion engine 1 is in a neighborhood of the recognition-operating point, i.e., when the difference between the current parameters (revolution rate and load) and recognition-operation-point parameters is "low" [i.e., lower than a threshold (as an absolute value)].

According to an embodiment, the intensity "S" of the noise generated by the internal-combustion engine 1 in the measurement-time window is preventively filtered by a band-pass filter or "A weighting" ("A averaging") filter, which is a particular type of equalization that enhances the frequencies mostly perceived by humans and cuts off those that are less audible).

During system calibration, the recognition-operating point is chosen to optimize (maximize) the existing differences between different fuels. In other words, the perceivable differences in the noise generated by the internal-combustion engine 1 as a function of the type of fuel used are less evident in some operating points and more evident in other operating points. To simplify the recognition of the type of fuel used, it is apparent that the recognition-operating points should be chosen in a zone in which the differences existing between different fuels are maximum. To increase the possibility of recognition, it is possible to use several comparison quantities "TH," each of which is associated with its own recognition-operating point different than the other recognition-operating points of the other comparison quantities "TH."

According to a first, simplified (and, thus, more robust) recognition method, the electronic-control unit 5 assigns a first value to the fuel feature if the synthetic index "I" is higher (lower) than the comparison quantity "TH" and assigns a second value, different than the first value, to the fuel feature if the synthetic index "I" is lower (higher) than the comparison quantity "TH." This first, simplified mode is of the "binary" type (i.e., includes the choice of two different values only as a function of the comparison between the synthetic index "I" and comparison quantity "TH"). According to a second, more refined (thus, at least potentially, less robust) recognition method, the electronic-control unit 5 calculates the value of the feature of the fuel by an interpolation performed as a function of the comparison between the synthetic index "I" and a comparison quantity "TH." In this second, more refined recognition method, at least two comparison quantities "TH" are normally used (which delimits a window in which the synthetic index "I" is found), and the feature of the fuel is determined by interpolating the fuel-feature values associated with the two comparison quantities "TH."

According to an embodiment, the electronic-control unit 5 calculates the FFT (Fast Fourier Transform) of the intensity "S" of the noise generated by the internal-combustion engine 1 in the measurement-time window and, thus, calculates the synthetic-index value "I" in the frequency domain as a function of the amplitude of at least one harmonic of the FFT. In some types of internal-combustion engines 1, the synthetic-index value "I" is only a function of the amplitude of the second harmonic of the FFT. In other words, the synthetic index "I" is equal to the energy level of the second harmonic of the FFT. In other types of internal-combustion engines 1, the value of the synthetic index "I" is only a function of the sum of the amplitudes of at least two even harmonics of the FFT (typically, the sum of the amplitudes of the second harmonic and fourth harmonics of the FFT). Alternatively, the value of the synthetic index "I" is a function only of the ratio between the amplitude of an even harmonic of the FFT and the amplitude of an odd harmonic of the FFT (e.g., the ratio between the amplitude of the second harmonic of the FFT and the amplitude of the first harmonic of the FFT) or is a function of only the ratio between the sum of amplitudes of at least two even harmonics of the FFT and the sum of the amplitudes of at least two odd harmonics of the FFT (e.g., the ratio between the sum of the amplitude of the second harmonic of the FFT and of the fourth harmonic of the FFT and the sum of the amplitude of the first harmonic of the FFT and of the third harmonic of the FFT). The value of the synthetic index "I" can also be correlated to the peak features of the amplitudes of the harmonics of the FFT (i.e., to how bigger and/or steeper is the difference between peak and valley in the spectrum of the harmonics of the FFT).

According to another embodiment, the electronic-control unit 5 calculates the synthetic index "I" directly as a function of the time variation of the noise intensity "S" of the internal-combustion engine 1 and, thus, calculates the value of the synthetic index "I" in the time domain. In this case, the synthetic index "I" is correlated to the timbre of the intensity "S" of the vibrations.

Constructive features of the internal-combustion engine 1 (e.g., number of cylinders, position and conformation of the exhausts, number and actuation of the valves, etc.) may considerably vary the generated noise timbre. Thus, a method for calculating the synthetic index "I" must be experimentally determined for each internal-combustion engine 1 (i.e., with which recognition of the sought feature can be optimized).

In the embodiment described above, the sensor used by the electronic-control unit is a microphone 6 and detects the intensity "S" of the noise generated by the internal-combustion engine 1. In another embodiment, the sensor used by the electronic-control unit 5 is an accelerometer 7, which is directly fitted on the internal-combustion engine 1 and detects the intensity "S" of the mechanical vibrations generated by the internal-combustion engine 1. In other words, to recognize the features of the fuel, the electronic-control unit 5 uses the intensity "S" of vibrations generated by the internal-combustion engine 1. Such vibrations may be acoustic (sound) vibrations (and, thus, detected by the microphone 6) or mechanical vibrations (and, thus, detected by the accelerometer 7). The mechanical vibrations generated by the internal-combustion engine 1 are closely correlated to the noise generated by the internal-combustion engine 1 because both are originated by the same physical phenomena generated by the fuel combustion in the cylinders 2.

According to an embodiment, the intensity "S" of the mechanical vibrations measured by the accelerometer 7 in the measurement-time window is preventively filtered by a band-pass filter that works in a window of 3-12 kHz (i.e., the band-pass filter attenuates the frequencies lower than 3 kHz and higher than 12 kHz and enhances the frequencies between 3 and 12 kHz).

According to an embodiment, the feature of the fuel that is recognized by the electronic-control unit 5 as a function of the intensity "S" of the vibrations generated by the internal-combustion engine 1 is the percentage of ethanol present in the fuel (obviously, for a spark-controlled internal-combustion engine 1 operating according to the "Otto" cycle). According to other embodiments, other features of the fuel can be determined—for example, the percentage of vegetable oils (such as rape-seed oil) present in the fuel (obviously, for a compression internal-combustion engine 1 operating according to the "diesel" cycle).

FIG. 2 is a chart illustrating the FFT of the intensity "S" of the noise generated by the internal-combustion engine 1 when the internal-combustion engine 1 uses two different types of fuel (a solid line indicates that the fuel consists of 100% ethanol while the dashed line indicates that the fuel consists of 22% ethanol and 78% petrol commercially known as "gasohol"). A difference occurs in the second harmonic of the FFT by varying the fuel type in FIG. 2. The difference of timbre of the noise generated by the internal-combustion engine 1 as the type of fuel varies is due to the fact that varying the type of fuel varies the dynamic of the combustion within the cylinders 2 and, consequently, vary (among other things) the combustion speed, pressure gradient inside the cylinders 2, and pressure inside the cylinders 2 as the exhaust valves open.

FIG. 3 is a chart illustrating the trend of the synthetic index "I" determined only as a function of the amplitude of the second harmonic of the FFT when the internal-combustion engine 1 uses two different types of fuel (a solid line indicates that the fuel consists of 100% ethanol while the dashed line indicates that the fuel consists of 22% ethanol and 78% petrol commercially known as "gasohol"). The left part of FIG. 3 shows the values of four synthetic indexes "I" calculated at four different engine-recognition points 1, 2, 3, 4 during normal operation. The right part of FIG. 3 shows the values of two synthetic indexes "I" calculated in two different engine-recognition points 5, 6 during an emergency operation ("recovery") in which a "lambda probe" arranged in the exhaust of the internal-combustion engine 1 is not working correctly.

In the recognition method described above, a "recovery" method may be used when the lambda probe present in the exhaust of the internal-combustion engine 1 is not working correctly. In other words, the fuel features are normally recognized by using the information provided by the lambda probe, and, in the case of malfunction of the lambda probe, the fuel features are recognized as a function of the recognition method, which does not include the use of the information provided by the lambda probe. Also, the recognition method may be used as a comparison sample with the same recognition performed using the information provided by the lambda probe to increase the recognition confidence. Furthermore, the recognition method can be easily implemented in an existing electronic-control unit 5 because it does not require a high additional computational burden. In addition, the recognition method allows for accurate and confident estimate of the features of the fuel actually used by the internal-combustion engine 1. Moreover, the recognition method is completely independent from the information provided by the lambda probe present in the exhaust of the internal-combustion engine 1 and, consequently, may be used both in "recovery" mode (when the lambda probe is not working correctly) and as a comparison sample for the recognition itself performed using the information provided by the lambda probe.

It should be appreciated by those having ordinary skill in the related art that the recognition method has been described above in an illustrative manner. It should be so appreciated also that the terminology that has been used above is intended to be in the nature of words of description rather than of limitation. It should be so appreciated also that many modifications and variations of the recognition method are possible in light of the above teachings. It should be so appreciated also that, within the scope of the appended claims, the recognition method may be practiced other than as specifically described above.

What is claimed is:

1. A method for recognizing at least one feature of fuel in an internal-combustion engine (1), said method comprising steps of:
    detecting, by at least one sensor, intensity (S) of vibrations generated by the internal-combustion engine (1) within a measurement-time window;
    determining a value of at least one synthetic index (I) by processing the intensity (S) of the vibrations generated by the internal-combustion engine (1) within the measurement-time window;
    comparing a synthetic index (I) with at least one predetermined comparison quantity (TH); and
    recognizing the feature of the fuel as a function of the comparison between the synthetic index (I) and comparison quantity (TH).

2. A recognition method according to claim 1, wherein said step of recognizing the feature of the fuel comprises further steps of:
    assigning a first value to the feature of the fuel if the synthetic index (I) is higher than the comparison quantity (TH); and
    assigning a second value different than the first value to the feature of the fuel if the synthetic index (I) is lower than the comparison quantity (TH).

3. A recognition method according to claim 1, wherein said step of recognizing the feature of the fuel comprises a further step of calculating the value of the feature of the fuel by an interpolation performed as a function of the comparison between the synthetic index (I) and comparison quantity (TH).

4. A recognition method according to claim 1, wherein said step of determining the value of the synthetic index (I) comprises further steps of:
    calculating FFT of the intensity (S) of the vibrations generated by the internal-combustion engine (1) within the measurement-time window; and
    calculating the value of the synthetic index (I) as a function of an amplitude of at least one harmonic of the FFT.

5. A recognition method according to claim 4, wherein the value of the synthetic index (I) is a function of the amplitude of a second harmonic of the FFT.

6. A recognition method according to claim 4, wherein the value of the synthetic index (I) is a function of a sum of the respective amplitudes of at least two even harmonics of the FFT.

7. A recognition method according to claim 6, wherein the value of the synthetic index (I) is a function of the sum of the respective amplitudes of a second harmonic of the FTT and a fourth harmonic of the FFT.

8. A recognition method according to claim 4, wherein the value of the synthetic index (I) is a function of a ratio between the amplitude of an even harmonic of the FFT and the amplitude of an odd harmonic of the FFT.

9. A recognition method according to claim 4, wherein the value of the synthetic index (I) is a function of a ratio between a sum of the respective amplitudes of at least two even harmonics of the FFT and a sum of the respective amplitudes of at least two odd harmonics of the FFT.

10. A recognition method according to claim 4, wherein the synthetic index is correlated with a feature of peak of the amplitude of the harmonic of the FFT.

11. A recognition method according to claim 1, wherein the synthetic index (I) is directly determined as a function of a variation in time of the intensity (S) of the vibrations generated by the internal-combustion engine (1) and correlated with timbre of the intensity (S) of the vibrations.

12. A recognition method according to claim 1, wherein said method comprises further steps of:
associating the comparison quantity (TH) to a given recognition-operating point of the internal-combustion engine (1); and
performing the comparison between the synthetic index (I) and comparison quantity (TH) when a current operating point of the internal-combustion engine is in a neighborhood of the recognition-operating point.

13. A recognition method according to claim 1, wherein the feature of the fuel is the percentage of ethanol present in the fuel.

14. A recognition method according to claim 1, wherein the sensor is a microphone (6) that detects the intensity (S) of noise generated by the internal-combustion engine (1).

15. A recognition method according to claim 1, wherein the sensor is an accelerometer (7) that detects the intensity (S) of mechanical vibrations generated by the internal-combustion engine (1).

* * * * *